(12) United States Patent
Silverman et al.

(10) Patent No.: US 8,557,552 B2
(45) Date of Patent: Oct. 15, 2013

(54) SELECTIVE NEURONAL NITRIC OXIDE SYNTHASE INHIBITORS

(75) Inventors: Richard B. Silverman, Northbrook, IL (US); Haitao Ji, Salt Lake City, UT (US); He Huang, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 13/441,683

(22) Filed: Apr. 6, 2012

(65) Prior Publication Data

US 2012/0258513 A1    Oct. 11, 2012

Related U.S. Application Data

(60) Provisional application No. 61/472,475, filed on Apr. 6, 2011.

(51) Int. Cl.
*C12N 9/99* (2006.01)
(52) U.S. Cl.
USPC .......................... 435/184; 546/256; 546/278.4
(58) Field of Classification Search
None
See application file for complete search history.

(56) References Cited

U.S. PATENT DOCUMENTS

| 7,740,790 B2 | 6/2010 | Onodera et al. |
| 7,994,326 B2 | 8/2011 | Silverman et al. |
| 2005/0107369 A1 | 5/2005 | Silverman et al. |
| 2008/0108814 A1 | 5/2008 | Silverman et al. |
| 2008/0176907 A1 | 7/2008 | Silverman et al. |
| 2010/0190230 A1 | 7/2010 | Silverman et al. |
| 2010/0292484 A1 | 11/2010 | Silverman et al. |

OTHER PUBLICATIONS

Hevel, Joan M., and Marietta, Michael A., "Nitric-Oxide Synthase Assays", Methods in Enzymology, vol. 233, 250-258, 1994.
Delker, Silvia L.; Ji, Haitao; Li, Huiying; Jamalm Joumana; Fang, Jianguo; Xue, Fengtian; Silverman, Richard B.; and Poulos, Thomas L., "Unexpected Binding Modes of Nitric Oxide Synthase Inhibitors Effective in the Prevention of a Cerebral Palsy Phenotype in an Animal Model", J. Am. Chem. Soc., 2010, 132, 5437-5442.
PCT Search Report from PCT/US2012/032595 issued on Oct. 12, 2012.

*Primary Examiner* — Noble Jarrell
*Assistant Examiner* — John S Kenyon
(74) *Attorney, Agent, or Firm* — Reinhart Boemer Van Deuren, s.c.

(57) ABSTRACT

Compounds and related methods for selective inhibition of neuronal nitric oxide synthase over inducible and endothelial isoforms, such compounds as can provide reduced cationic character and enhanced bioavailability.

30 Claims, 3 Drawing Sheets

Additional Series D Target Molecules
Y = CH$_2$CH$_2$, CH=CH

Additional Series C Target Molecules
Y = CH$_2$CH$_2$, CH=CH

SELECTIVE NEURONAL NITRIC OXIDE SYNTHASE INHIBITORS

This application claims priority benefit from provisional application No. 61/472,475 filed Apr. 6, 2011, which is incorporated herein by reference in its entirety.

This invention was made with government support under GM049725 awarded by the National Institutes of Health. The government has certain rights in the invention.

BACKGROUND OF THE INVENTION

Neuronal nitric oxide synthase (nNOS) catalyzes the oxidation of L-arginine to L-citrulline in the central nervous system, generating nitric oxide (NO), a critical neurotransmitter. Significant research has implicated the overexpression of nNOS— and overproduction of NO—in various neurological diseases, including Parkinson's, Alzheimer's, and Huntington's diseases, as well as neuronal damage due to stroke. Inhibiting endothelial nitric oxide synthase (eNOS) and inducible nitric oxide synthase (iNOS) is, however, undesirable, because these isozymes are responsible for maintaining crucial body function. Thus, selective inhibition of nNOS over its closely related isoforms, eNOS and iNOS, can provide a promising strategy in developing therapeutics for the treatment of neurodegenerative diseases.

Through on-going research of nNOS selective inhibitors, a pyrrolidine-based compound with an enthanamino linker moiety (cpd JI10, discussed below) was found to provide great potency ($K_i$=15 nM) and very high selectivity for nNOS over eNOS (2100 fold) and iNOS (630 fold). However, despite the promising inhibitory activity of this compound, further application to neurodegenerative therapeutics has been impeded by several structural characteristics. First, the flexible m-fluorophenyl ethanamino tail brought multiple rotatable bonds to the inhibitor, limits its potency and selectivity. In addition, the benzylic position of the m-fluorophenyl ring is highly susceptible to metabolic oxidation reactions. More importantly, positive charge at physiological pH, relating to the two amino groups—including one group in the aforementioned ethanamino linker, decreases the chance of such a compound to penetrate the blood brain barrier (BBB).

SUMMARY OF THE INVENTION

In light of the foregoing, it is an object of the present invention to provide compounds, compositions and related methods of use for the selective inhibition of neuronal nitric oxide synthase, thereby overcoming various deficiencies and shortcomings of the prior art including those outlined above. It would be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is an object of the present invention to provide one or more small molecule and/or non-peptide compounds exhibiting selective nNOS inhibition over other enzyme isoforms and providing improved membrane permeability and bioavailability.

It can be another object of the present invention to provide a rationally-designed compound to affect binding orientation and improved potency and selectivity.

It can be another object of the present invention, alone or in conjunction with one or more of the preceding objectives, to reduce basicity of such a compound, as can be accomplished by removal of the aforementioned ethanamino linker moiety, to reduce molecular cationic character at physiological pH and to enhance bioavailability by improved penetration of the BBB.

It can be another object of the present invention to provide one or more such non-peptide compounds for in vitro use and study under conditions promoting nitric oxide production, indicative of one or more mammalian disease states.

Alternatively, it can also be an object of the present invention to provide one or more such compounds enabling in vivo treatment of such disease states.

Other objects, features, benefits and advantages of the present invention will be apparent from this summary and the following descriptions of certain embodiments of such compounds, compositions and/or methods and will be readily apparent to those skilled in the art having knowledge of the synthetic techniques described herein. Such objectives, features, benefits and advantages will be apparent from the above as taken into conjunction with the accompanying examples, data, figures and references incorporated herein, together with all reasonable inferences to be drawn therefrom.

In part, the present invention can relate to compounds of a formula

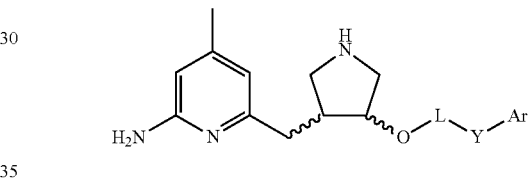

wherein L can be a linker moiety selected from quinolinylene, isoquinolinylene, naphthylenylene, methylene, ethylene, trimethylene, tetramethylene and pentamethylene moieties; Y can be selected from $CH_2CH_2CH_2$, $CH_2$ —CH=CH—, O, NH and a covalent bond, providing Y is NH or a covalent bond when L is quinolinylene, isoquinolinylene or naphthylenylene; and Ar can be independently selected from mono- and multi-substituted aryl or heteroaryl moieties, wherein such heteroatom(s) can be selected from O, N, S and combinations thereof, such substituents selected from amino, methyl, methoxy, fluoro, chloro, and mono-, di- and trifluoromethyl, and mono-, di- and trichloromethyl substituents, and combinations thereof. In certain non-limiting embodiments, Ar can be selected from naphthyl, phenyl and pyridinyl moieties. Regardless of Ar identity, such a moiety can be mono- or multi-substituted.

More generally, such compounds can be considered in the context of mitigation or partial removal of a degree of positive charge therefrom, as compared to inhibitor compounds of the prior art, such as at physiological pH. Accordingly, without limitation, in certain such embodiments, such a compound can be present as an acid salt, either partially or fully protonated. In certain such embodiments, the counter ion(s) can bea conjugate base of a protic acid. Regardless, such an aryl/heteroaryl moiety and/or substituent(s) thereon can be selected from moieties capable of contribution to or effect on enzyme binding or interaction.

In part, the present invention can be directed to compounds of a formula

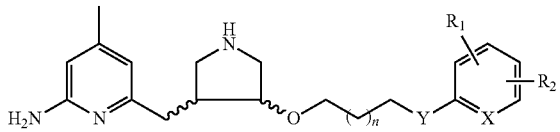

wherein n can be selected from 0 and 1; Y can be independently selected from $CH_2$, O, NH, $CH_2O$, $CH_2NH$, $CH_2CH_2$ and CH=CH moieties; X can be independently selected from N and CH; and $R_1$ and $R_2$ can be independently selected from H, amino, methyl, methoxy, fluoro, chloro, and mono-, di- and trifluoromethyl, and mono-, di-, and trichloromethyl substituents, and combinations thereof.

In certain non-limiting embodiments, such a compound can be selected from compounds of a formula

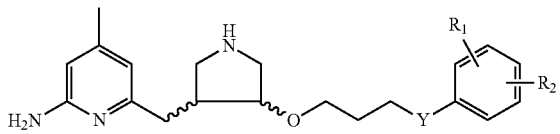

wherein Y can be selected from $CH_2CH_2$ and CH=CH moieties; and $R_1$ and $R_2$ can be independently selected from H, Cl and F regardless of ring position. In certain other embodiments, such a compound can be selected from compounds of a formula

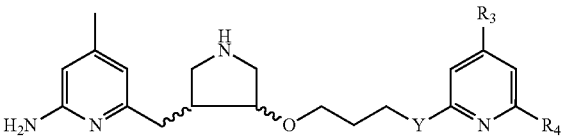

wherein Y can be independently selected from $CH_2CH_2$ and CH=CH moieties; $R_3$ can be selected from H and $CH_3$; and $R_4$ can be independently selected from H and $NH_2$. As discussed above, any stereocenter can be (S) or (R) with respect to any other stereocenter(s), whether such a compound is present as a salt, hydrate or solvate, whether or not the corresponding entantiomers are resolved.

In part, the present invention can also provide a method of affecting and/or inhibiting a nitric oxide synthase. Such a method can comprise contacting, in vivo or in vitro, a nitric oxide synthase with an effective amount of any one or more of the present compounds, including, but not limited to those illustrated by the following examples, referenced figures and/or accompanying synthetic schemes. Such a method can comprise providing a compound or a related composition of this invention; and contacting a nitric oxide synthase enzyme with such a compound/composition, such contact as can selectively inhibit neuronal nitric oxide synthase over inducible and/or endothelial isoforms.

DETAILED DESCRIPTION OF CERTAIN EMBODIMENTS.

Certain embodiments of this invention can be considered in the context of and with comparison to prior studies on NOS inhibition. Synthetic routes for prior art compounds JI10 and difluoro-JI10 are shown in Schemes 1A and 1B, respectively.

The synthesis of JI10 has been described previously in the literature. One modification relates to the deprotection of the Bn group by catalytic hydrogenation using $Pd(OH)_2/C$ as the catalyst. The typical protocol was 200 mg of 20% $Pd(OH)_2$ on carbon for 50 mM of the starting material, and 1.5 equivalent of HOAc as an additive. Here, the reaction was stirred at 60° C. in ethanol for 18 h under one atmosphere of hydrogen. The yield of the product was significantly increased to 90%. The synthesis of racemic difluoro-JI10 has also been published. The original reported synthesis used $Pd(OH)_2/C$, 500 psi $H_2$, 2:1 EtOH/HCl (12 N), rt, 40 h. Here, catalytic conditions included $Pd(OH)_2/C$, under 1 atm $H_2$, in EtOH, at 60° C., for 18 h.

Both JI10 and difluoro-JI10 were synthesized with a yield of 50 mg and used for comparative pharmacokinetic and BBB permeability studies, together with several representative compounds of this invention.

Scheme 1.

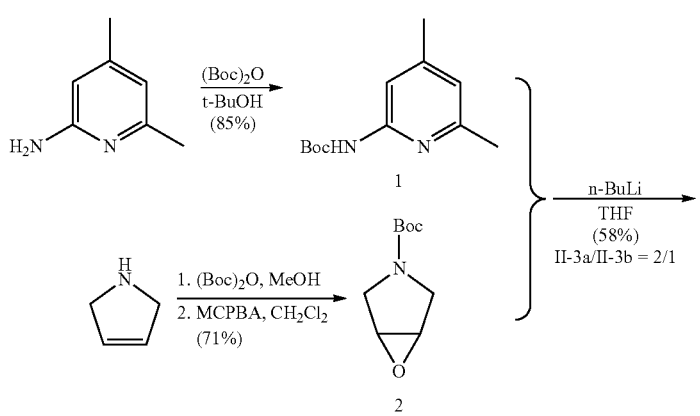

-continued
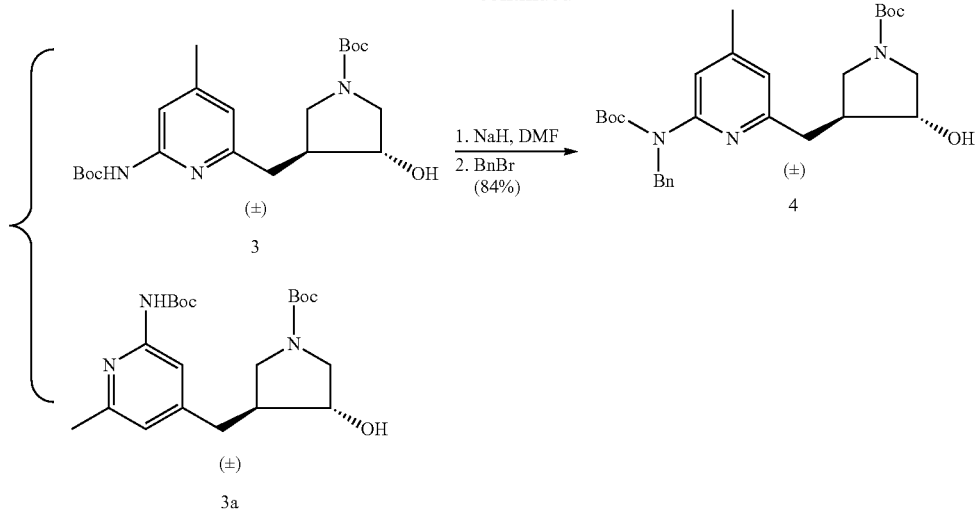
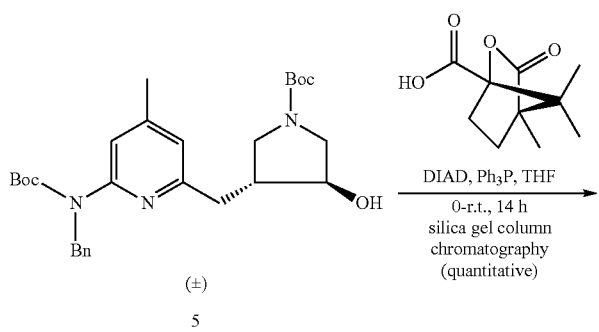
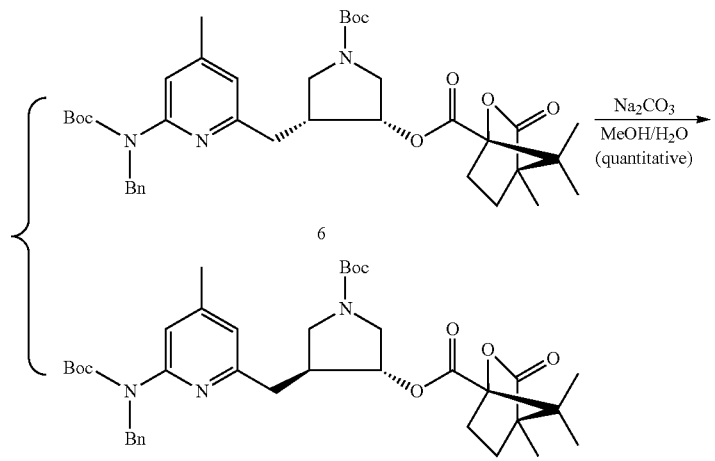
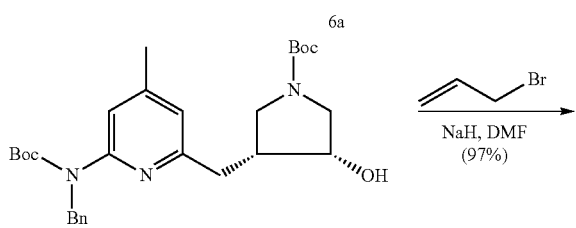

-continued
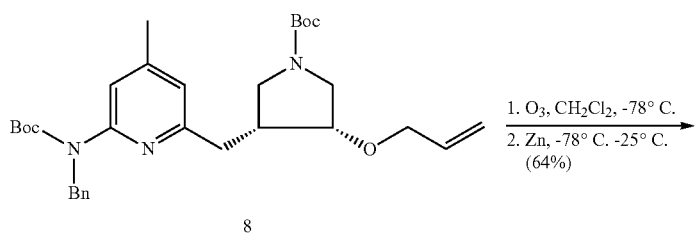
8
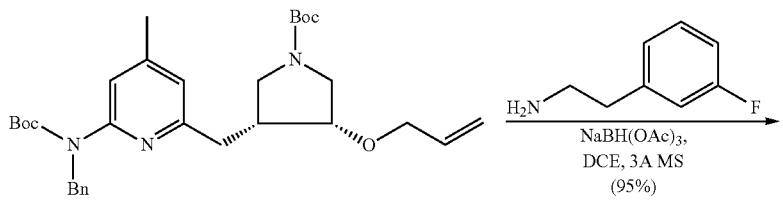
9
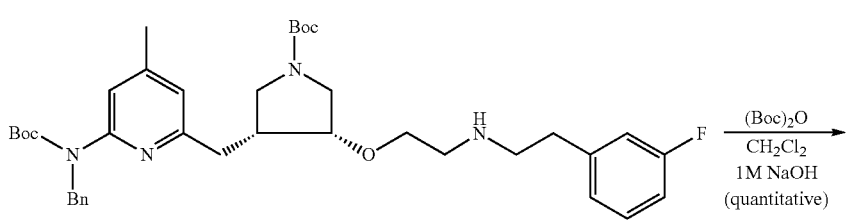
10
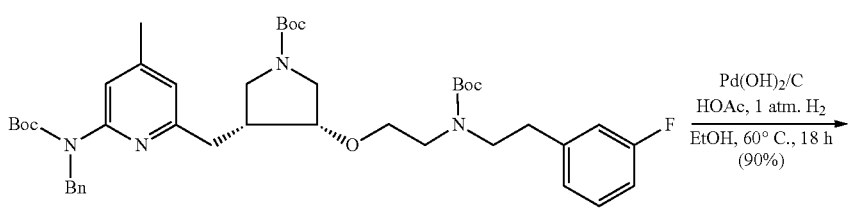
11
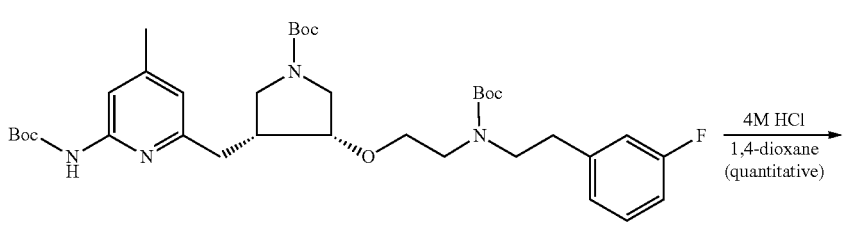
12
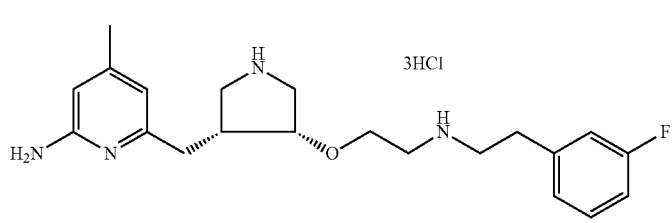
JI10

-continued
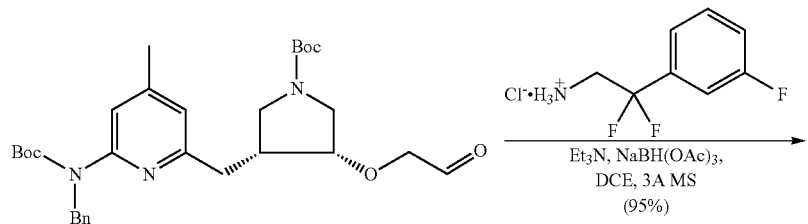
9
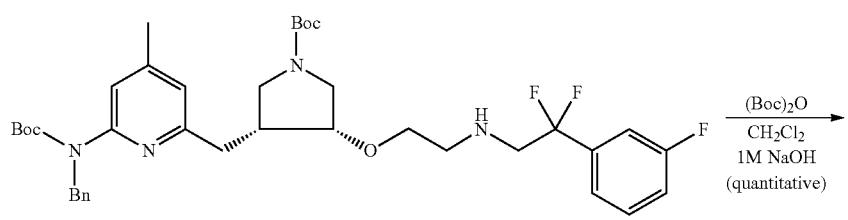
13
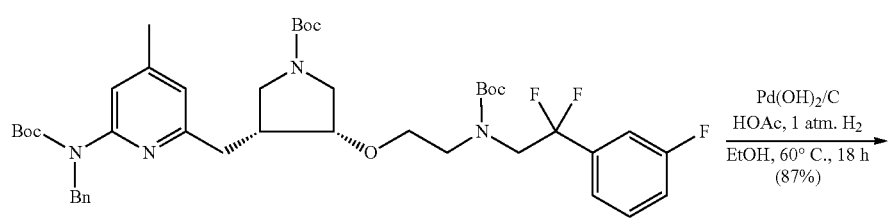
14
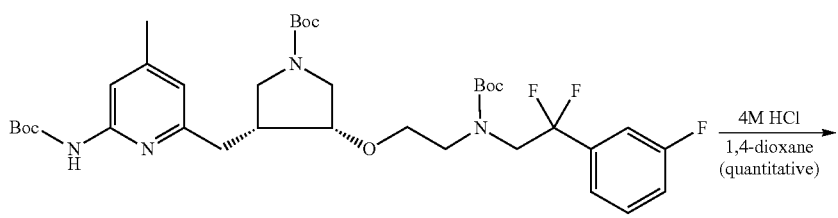
15
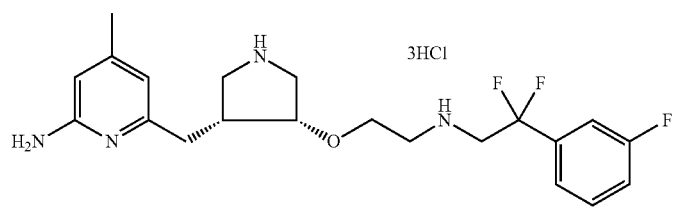
difluoro-JI10

The crystal structure of nNOS complexed with JI10 shows that the binding conformation of JI10 adopts a 180° flipped-over conformation compared to that of JI9, the enantiomer of JI10. (See, Telker, S. L.; Ji, H.; Li, H.; Jamal, J.; Fang, J.; Xue, F.; Silverman, R. B.; Poulos, T. L. Unexpected Binding Modes of Nitric Oxide Synthase Inhibitors Effective in the Prevention of a Cerebral Palsy Phenotype in an Animal Model. *J. Am. Chem. Soc.* 2010, 132(15), 5437-5442.) Realization of a new binding mode of JI10 with nNOS provided an opportunity to consider removal of the secondary amine on the 3-fluorophenethylamino side chain, and design inhibitors with increased BBB permeability.

Figure 1:
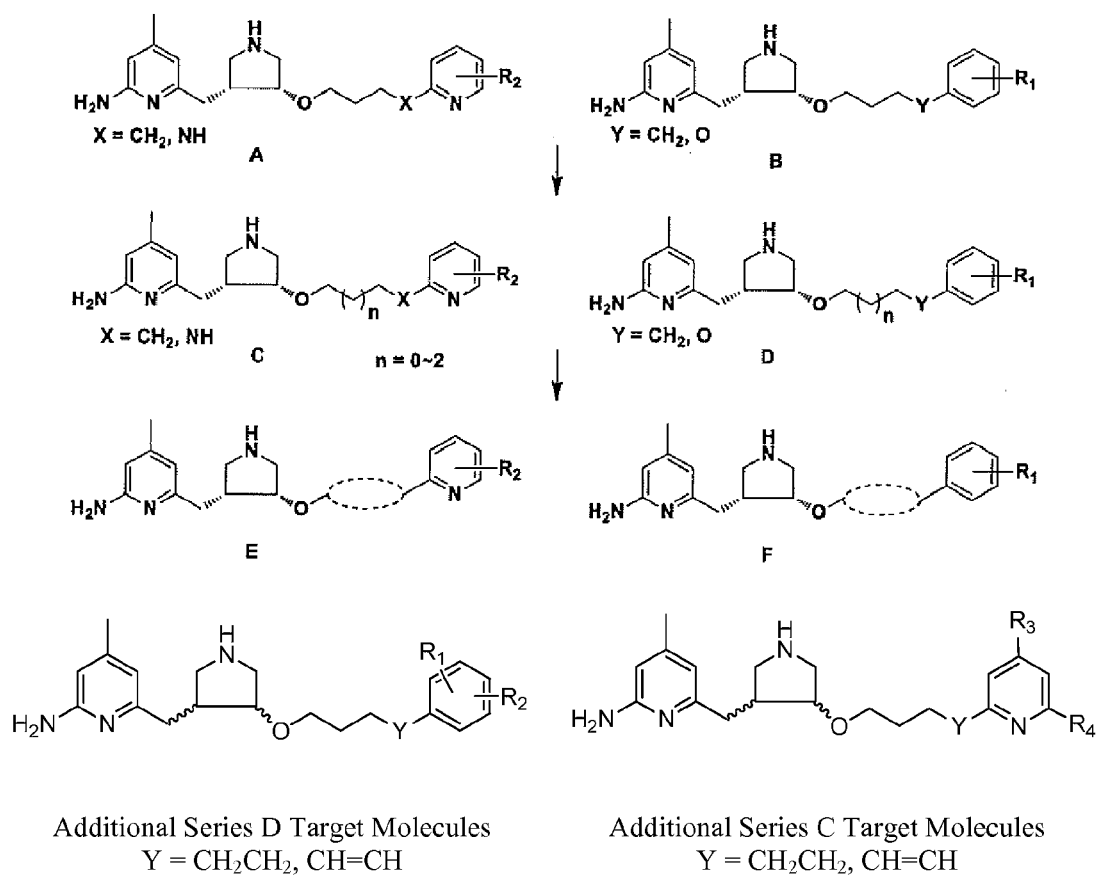
FIG. 1. Schematic chemical structures of representative, non-limiting selective nNOS inhibitors, target Series A-F, in accordance with certain embodiments of this invention.

A rational design of monocationic derivatives—based on such a flipped-over binding mode of JI10 to the induced-fit nNOS—can be envisioned in conjunction with the chart and target molecules in FIG. 1. With regard to one or more possible design aspects, several modifications were considered: appropriate substituents on the aromatic ring of the right side of the compounds in FIG. 1; the need to stretch or shorten the length of molecules by insertion or deletion of some heteroatoms and to maximize the binding affinity of the ligand with the active site; and cyclization of the linker moiety by the introduction of the various ring systems, such as cyclopropyl, cyclobutyl, cyclopentyl or cyclohexyl rings, between the pyrrolidine ring and the aromatic ring on the right side of the molecules.

A synthetic route for target molecule A (FIG. 1) is shown in Scheme 2. Compound 8 was subjected to hydroboration with 9-borabicyclo-[3.3.1]nonane (9-BBN), and subsequent alkaline oxidation with $H_2O_2$ to afford 16 in an 81% yield. The N-benzyl group of 16 was removed in an 89% yield by catalytic hydrogenation using $Pd(OH)_2$ on carbon as the catalyst and HOAc as an additive. The hydroxyl group of 17 was oxidized to aldehyde 18 with Dess-Martin periodinane in an 82% yield, and then a Wittig reaction was used to generate 20. The alkene group of 20 was reduced to a single bond by atalytic hydrogenation; deprotection of the Boc group afforded the final product (22). Deprotection of the Boc group of 20 generated final product 23.

Scheme 2.

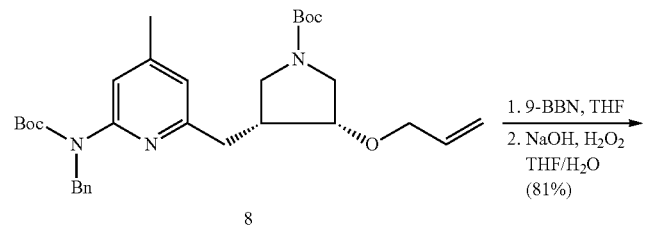

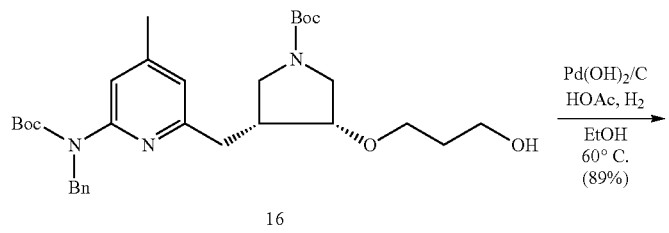

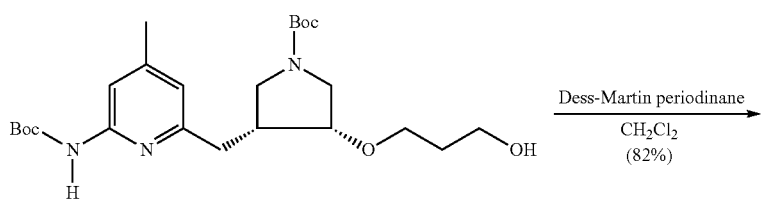

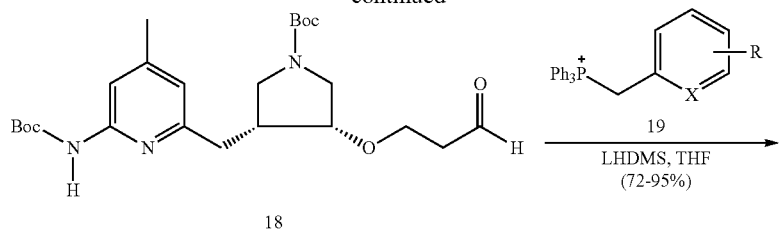
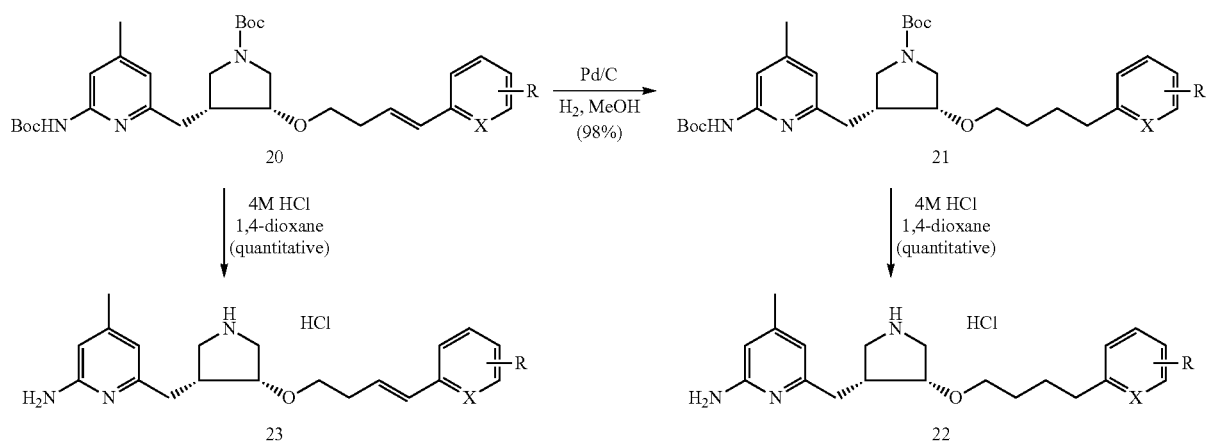
Four representative compounds (22a-22c, 23) have been prepared based on the synthetic route of Scheme 2.
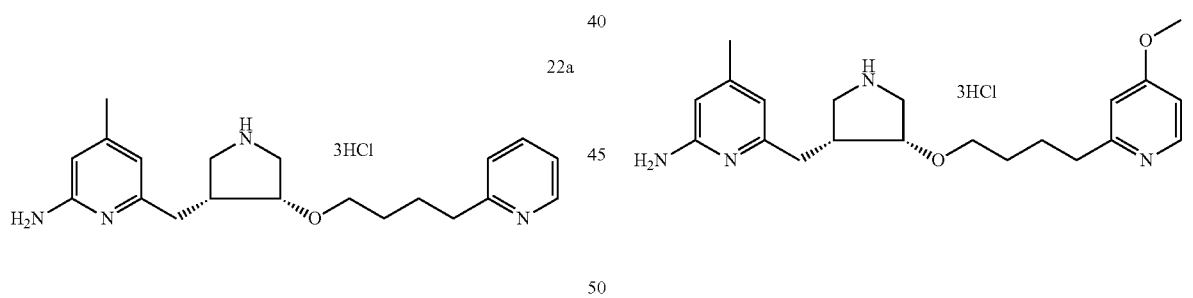
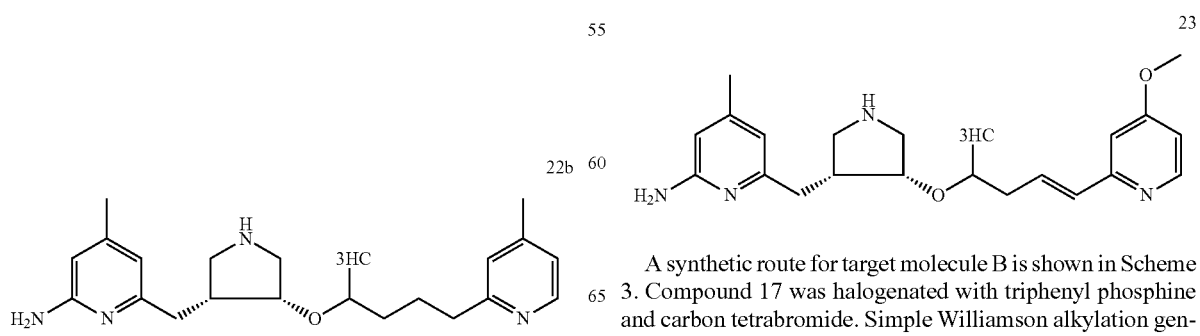
A synthetic route for target molecule B is shown in Scheme 3. Compound 17 was halogenated with triphenyl phosphine and carbon tetrabromide. Simple Williamson alkylation generated 24. Deprotection of the Boc group generated 25.

Scheme 3.

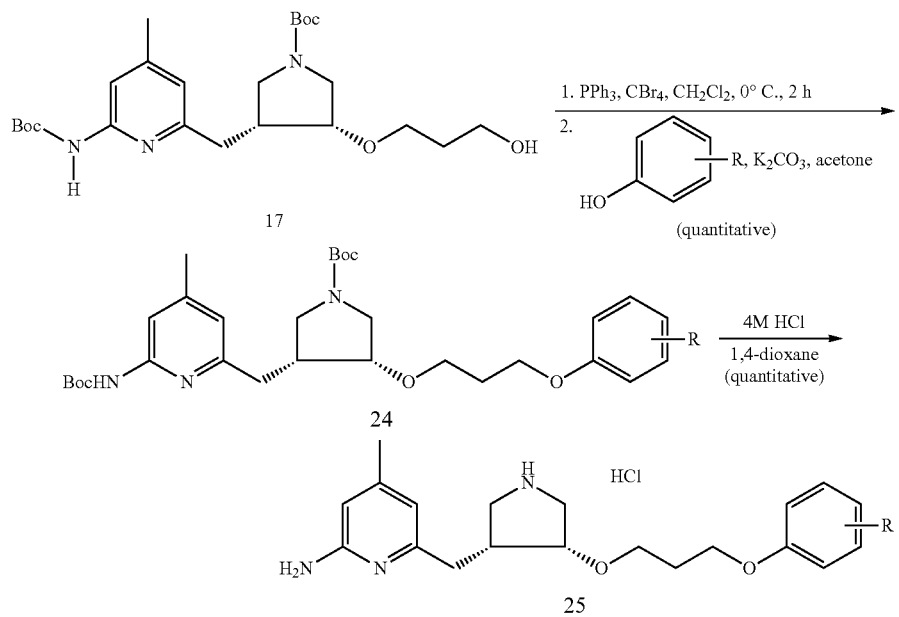

On the basis of the synthetic route in Scheme 3, six representative compounds (25a-25f) have been prepared.

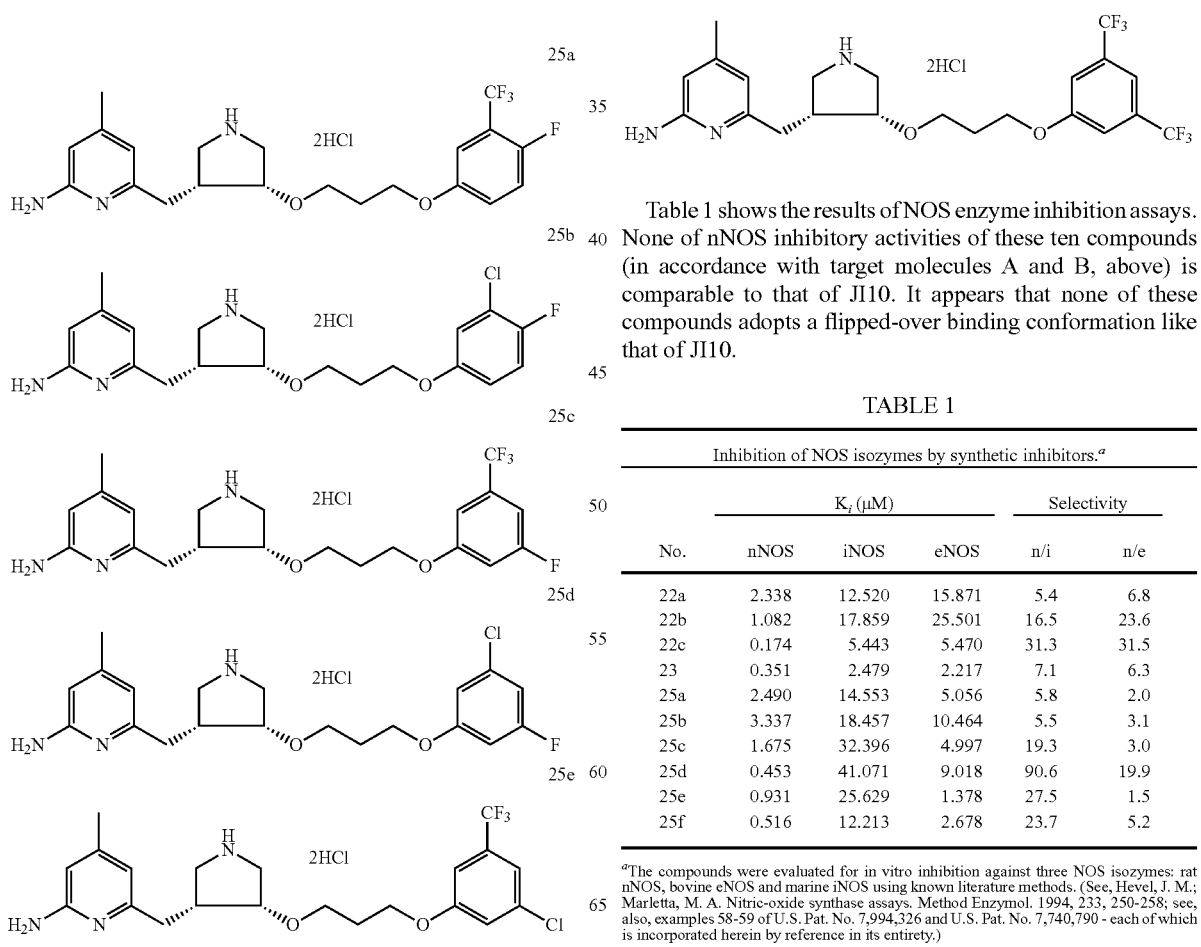

Table 1 shows the results of NOS enzyme inhibition assays. None of nNOS inhibitory activities of these ten compounds (in accordance with target molecules A and B, above) is comparable to that of JI10. It appears that none of these compounds adopts a flipped-over binding conformation like that of JI10.

TABLE 1

Inhibition of NOS isozymes by synthetic inhibitors.[a]

| No. | $K_i$ (μM) | | | Selectivity | |
|---|---|---|---|---|---|
| | nNOS | iNOS | eNOS | n/i | n/e |
| 22a | 2.338 | 12.520 | 15.871 | 5.4 | 6.8 |
| 22b | 1.082 | 17.859 | 25.501 | 16.5 | 23.6 |
| 22c | 0.174 | 5.443 | 5.470 | 31.3 | 31.5 |
| 23 | 0.351 | 2.479 | 2.217 | 7.1 | 6.3 |
| 25a | 2.490 | 14.553 | 5.056 | 5.8 | 2.0 |
| 25b | 3.337 | 18.457 | 10.464 | 5.5 | 3.1 |
| 25c | 1.675 | 32.396 | 4.997 | 19.3 | 3.0 |
| 25d | 0.453 | 41.071 | 9.018 | 90.6 | 19.9 |
| 25e | 0.931 | 25.629 | 1.378 | 27.5 | 1.5 |
| 25f | 0.516 | 12.213 | 2.678 | 23.7 | 5.2 |

[a]The compounds were evaluated for in vitro inhibition against three NOS isozymes: rat nNOS, bovine eNOS and marine iNOS using known literature methods. (See, Hevel, J. M.; Marletta, M. A. Nitric-oxide synthase assays. Method Enzymol. 1994, 233, 250-258; see, also, examples 58-59 of U.S. Pat. No. 7,994,326 and U.S. Pat. No. 7,740,790 - each of which is incorporated herein by reference in its entirety.)

In light of such results, it was thought that the length of the side chains in 22a-22c, 23, 25a-25f was not long enough to reach two "hot spots": One close to Glu592 in the S pocket, and the other close to heme propionate D in the C1 pocket, which is created by the induced fit of nNOS. Accordingly, derivatives with a side chain one carbon longer (target molecules C and D, FIG. 1) were designed.

Synthetic routes for variations of target molecule C are shown in Schemes 4A-C, respectively. Compounds Ji18 and Ji19 in FIG. 2 were synthesized based on Scheme 4A. Compounds Ji20 and Ji21 in FIG. 2 were synthesized based on Scheme 4B.

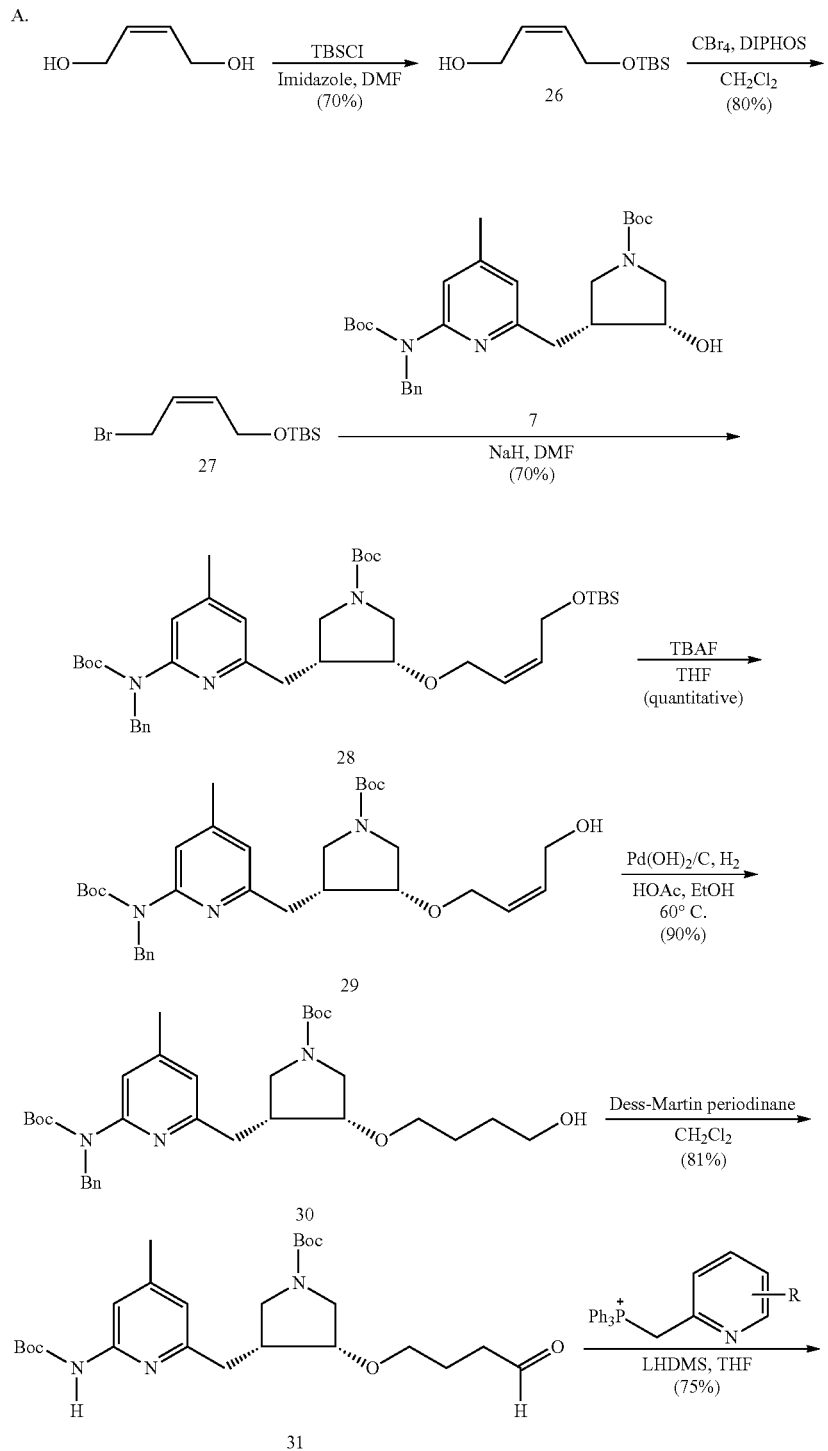

-continued
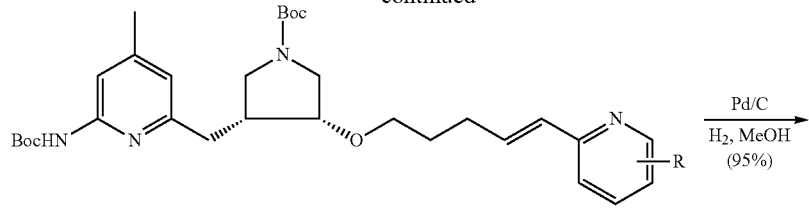
32
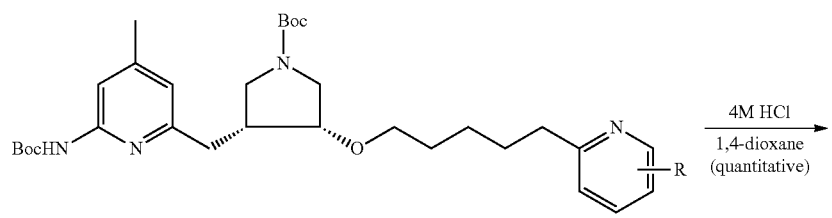
33
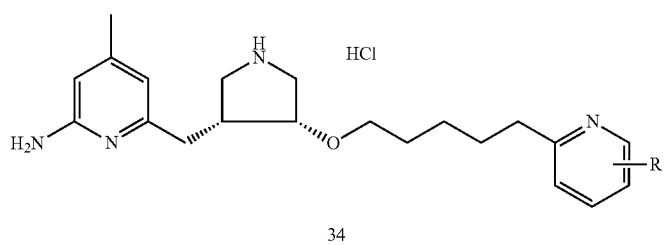
34
B.
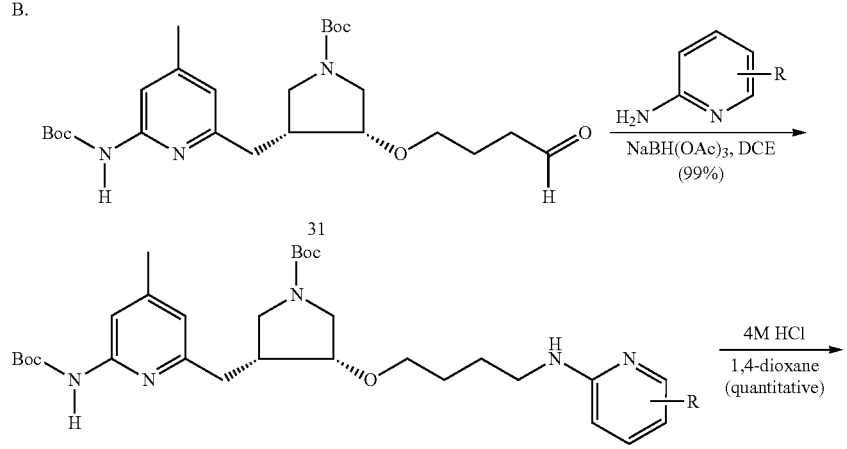
31
35
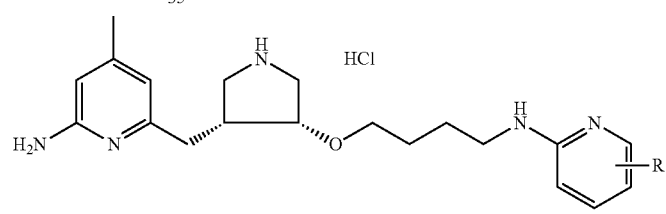
36

Figure 2:
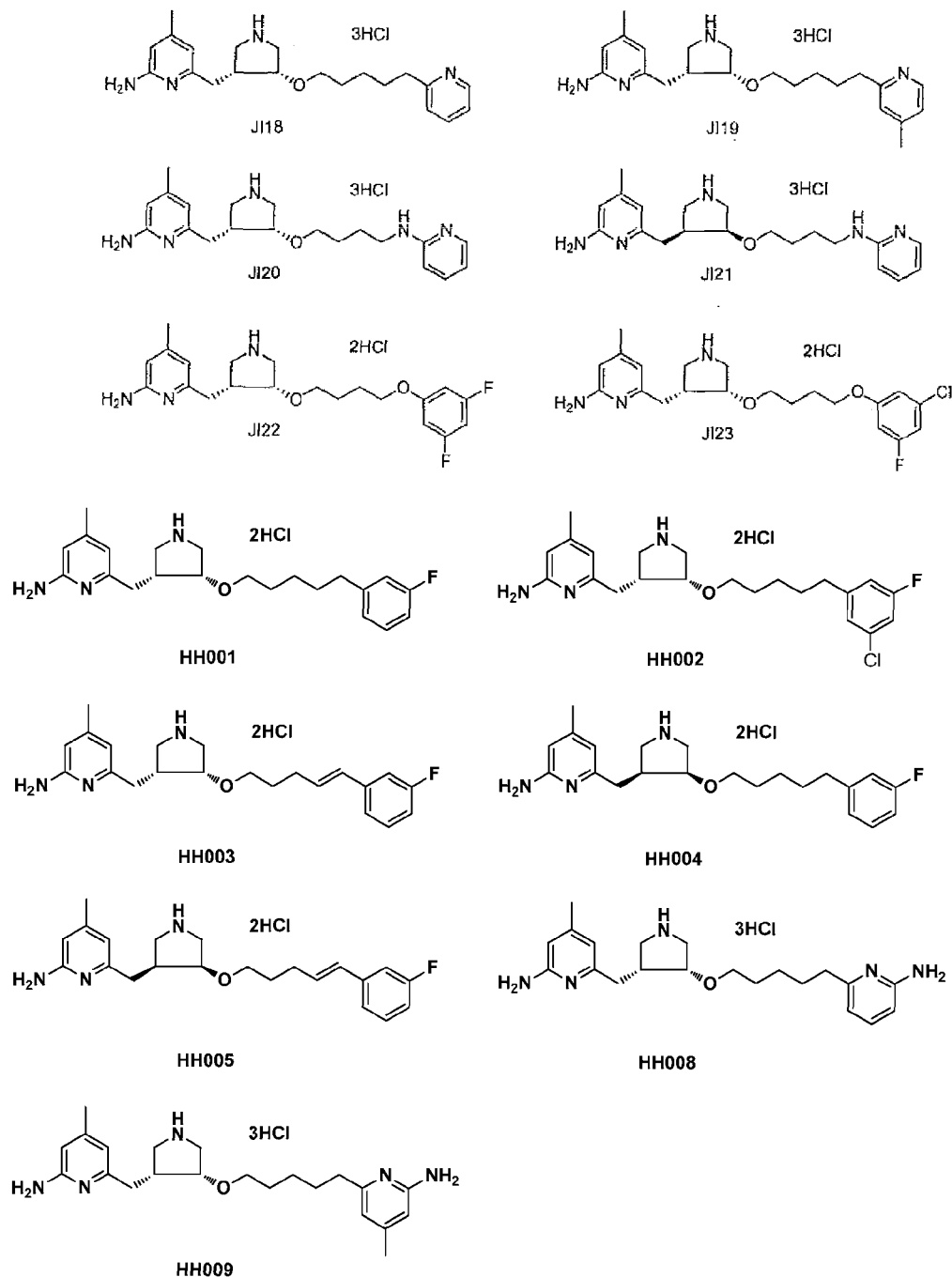
FIG. 2. Representative non-limiting inhibitor compounds, in accordance with certain embodiments of this invention.

More specifically, compounds HH008 and HH009 in FIG. 2 were synthesized base on Scheme 4C, below. Boc-protected 2-aminopyridine analogs were treated with n-butyllithium and allowed to react with (Z)-((4-bromobut-2-en-1-yl)oxy)(tert-butyl)dimethylsilane. The amino groups of the products were further protected with benzyl groups. The TBS protecting group was then removed, followed by bromination to form the allyl bromide intermediates. Subsequent nucleophilic substitution of the pyrrolidinyl alcohol (see, compound 7, Schemes 1 and 4A) and debenzylation, with concomitant double bond reduction, gave the corresponding ethers. Finally, removal of the Boc-protecting group proceeded smoothly, giving high yields of the compounds HH008 and HH009 (FIG. 2, R=H and CH$_3$, respectively).

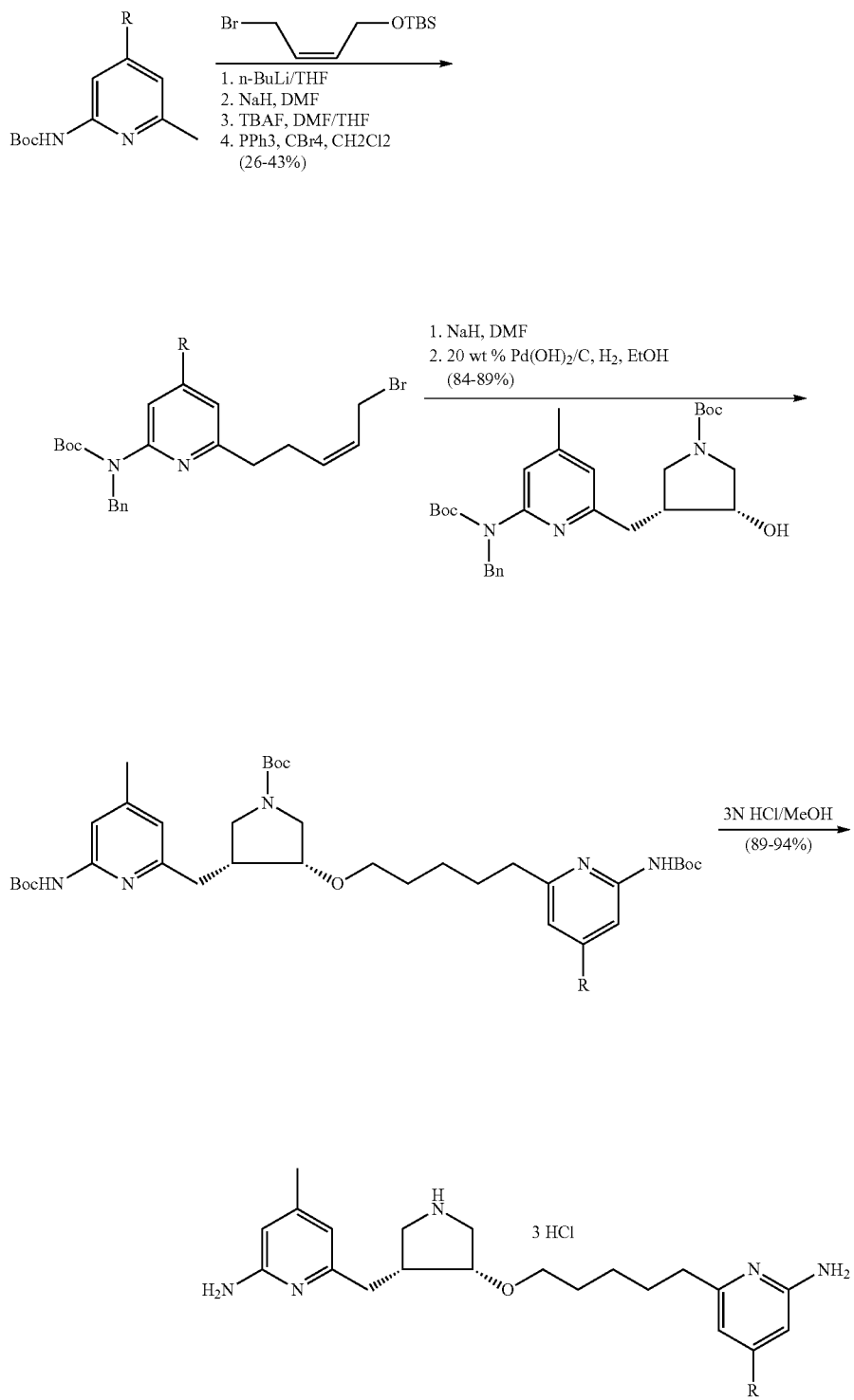

A synthetic route for target molecule D compound is shown in Scheme 5A. Two final products (Ji22 and Ji23 in FIG. 2) were synthesized based on this route.

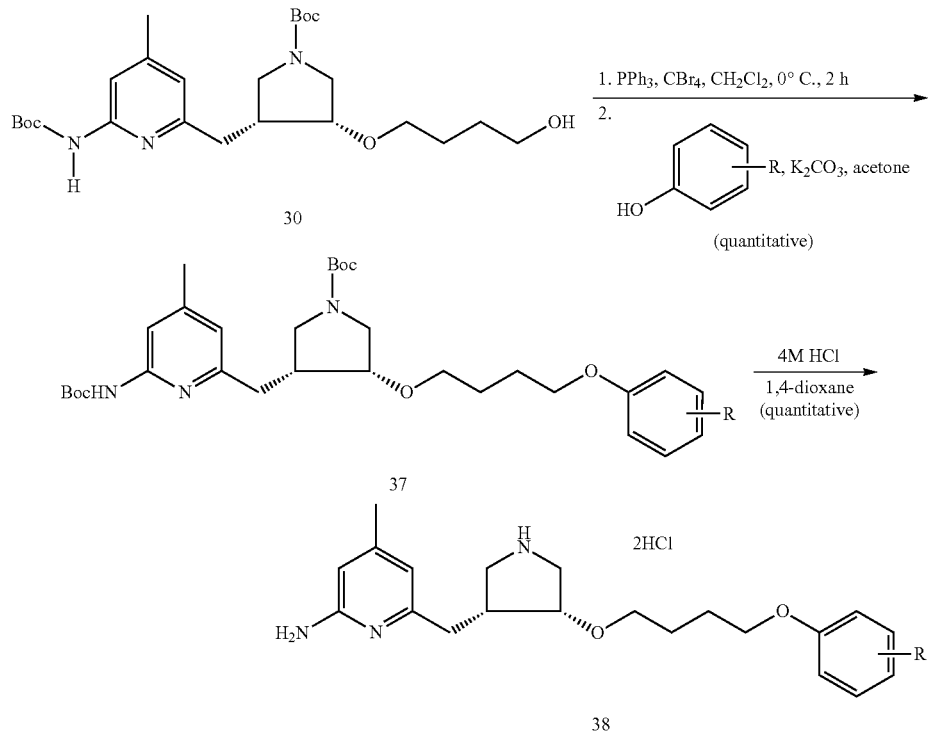

Scheme 5A.

More specifically, compounds HH001-HH005 in FIG. 2 were synthesized based on Scheme 5B, below. A single pyrrolidinyl alcohol enantiomer was treated with NaH, and the resulting anion was allowed to react with (Z)-(((4-bromobut-2-en-1-yl)oxy)-methyl)benzene. Catalytic hydrogenation of the crude product removed the benzyl-protecting group and also reduced the double bond, giving a high yield of the ether alcohol. Oxidation gave the aldehyde, and Wittig reaction with the corresponding phosphorus ylides allowed the isolation of the intermediate alkenes in moderate yields. Finally, double bond reduction followed by Boc-deprotection gave corresponding compounds HH001-HH005 (FIG. 2).

Scheme 5B.

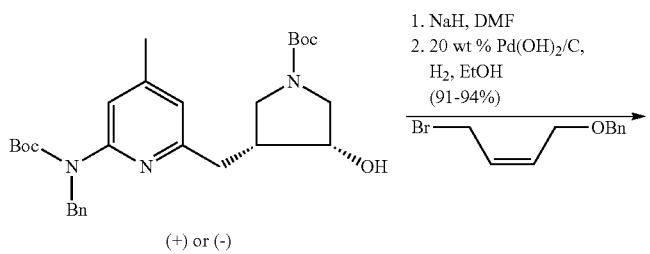

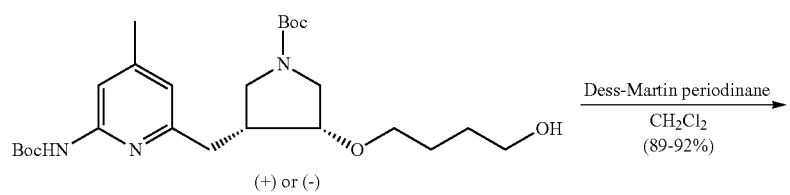

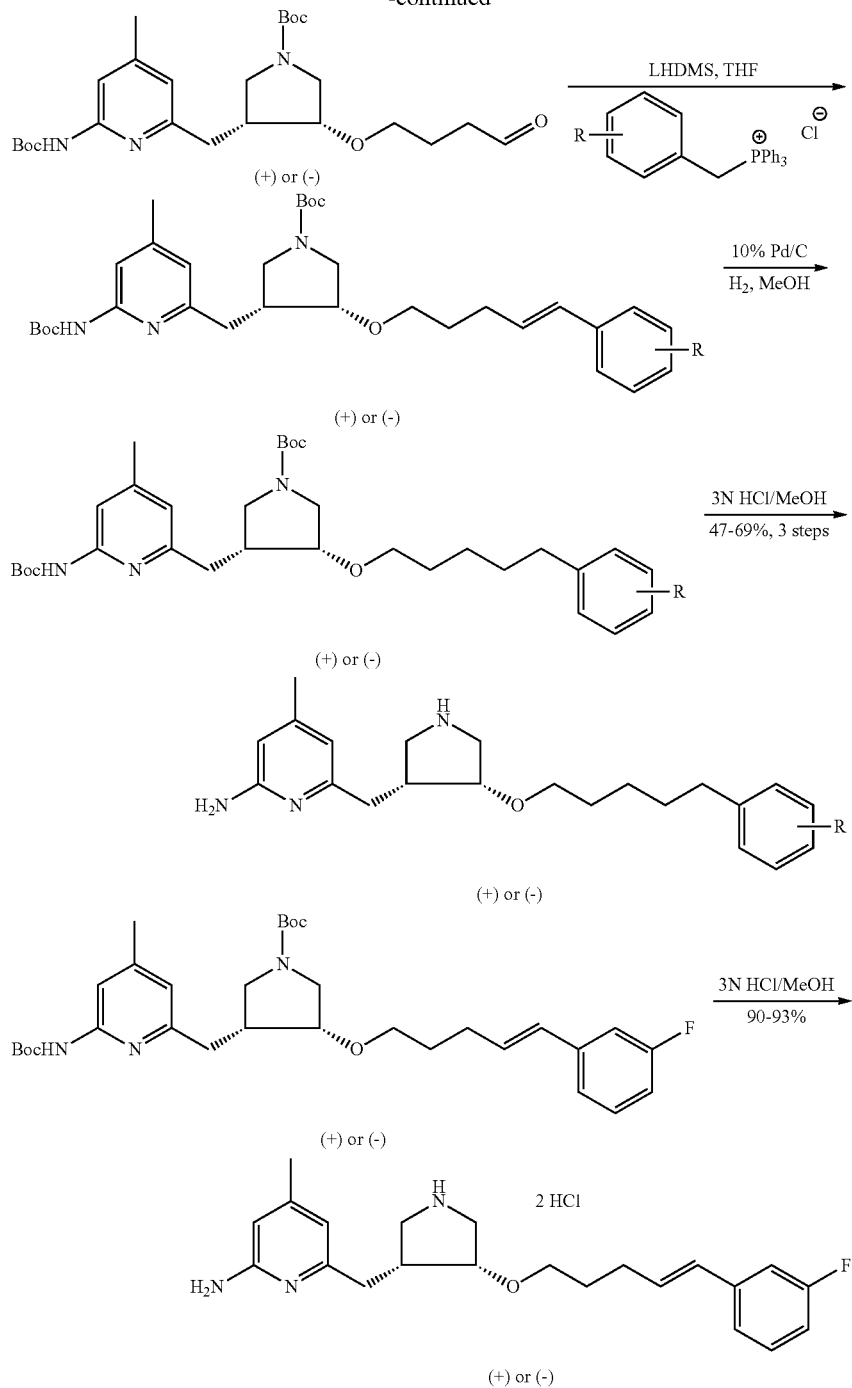

Figure 3:
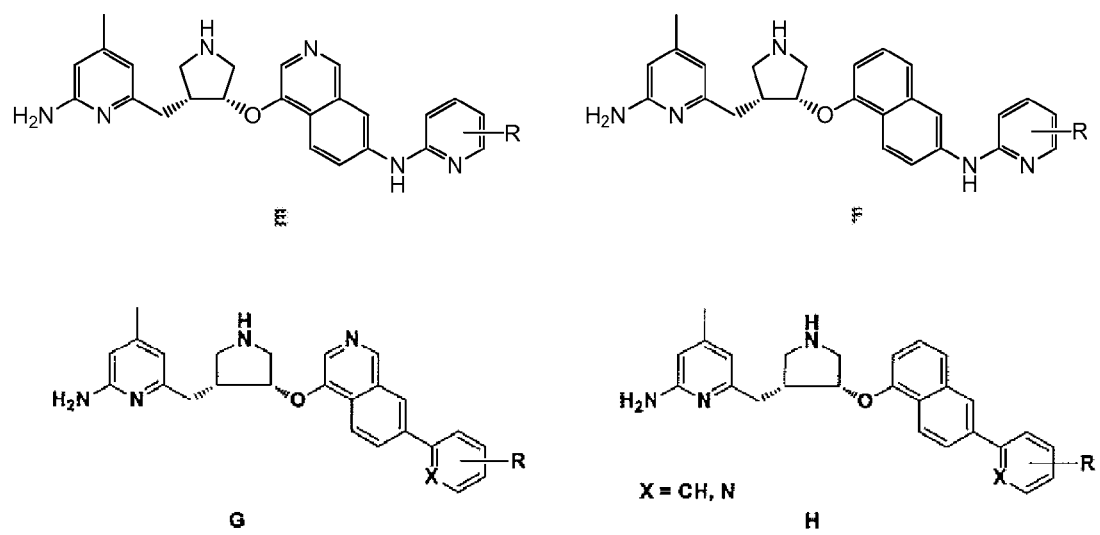
FIG. 3. Chemical structures of representative, non-limiting inhibitor compounds, in accordance with certain embodiments of this invention.

Relating to target molecules E and F (FIG. 1) consider compounds G and H (FIG. 3). However, it was shown by the biological tests of the biphenyl and phenoxyphenyl analogues that G and H are not especially useful—a reason for which may be that the side chain is one atom shorter than that required by the enzyme active site. If this hypothesis is correct, compounds E and F should be able to flip over in the active site.

The synthesis of an E series target compound (FIG. 1) is shown in Schemes 6A-C. Compound 40 was synthesized according to literature procedures. (See, Telker, S. L.; Ji, H.; Li, H.; Jamal, J.; Fang, J.; Xue, F.; Silverman, R. B.; Poulos, T. L. Unexpected Binding Modes of Nitric Oxide Synthase Inhibitors Effective in the Prevention of a Cerebral Palsy Phenotype in an Animal Model. *J. Am. Chem. Soc.* 2010, 132(15), 5437-5442; and Scheme 6A.) The synthesis of 45 has been done as shown in Scheme 6B. Reductive amination of 3-bromobenzaldehyde with glycine methyl ester generated 41, in quantitative yield with triethylamine as the base, sodium borohydride as the reducing reagent, and methanol as the solvent. The secondary amino group of 41 was tosylated, and hydrolysis of the methyl ester afforded 43 in a quantitative yield. Intramolecular cyclization of 43 was achieved by a classical Friedel-Crafts reaction. The desired compound (44)

and the ortho-cyclized by-product (44a) were separated by silica gel column chromatography in a 77% and 7% yield, respectively. Deprotection of the tosyl group and subsequent oxidation generated the aromatic compound (45) in a 86% yield. A Buchwald-Hartwig reaction generates compound 46, and subsequent Mitsunobu reaction (Scheme 6C) generates intermediate 47. Deprotection of the Bn and Boc groups afford desired final product 49.

Scheme 6.

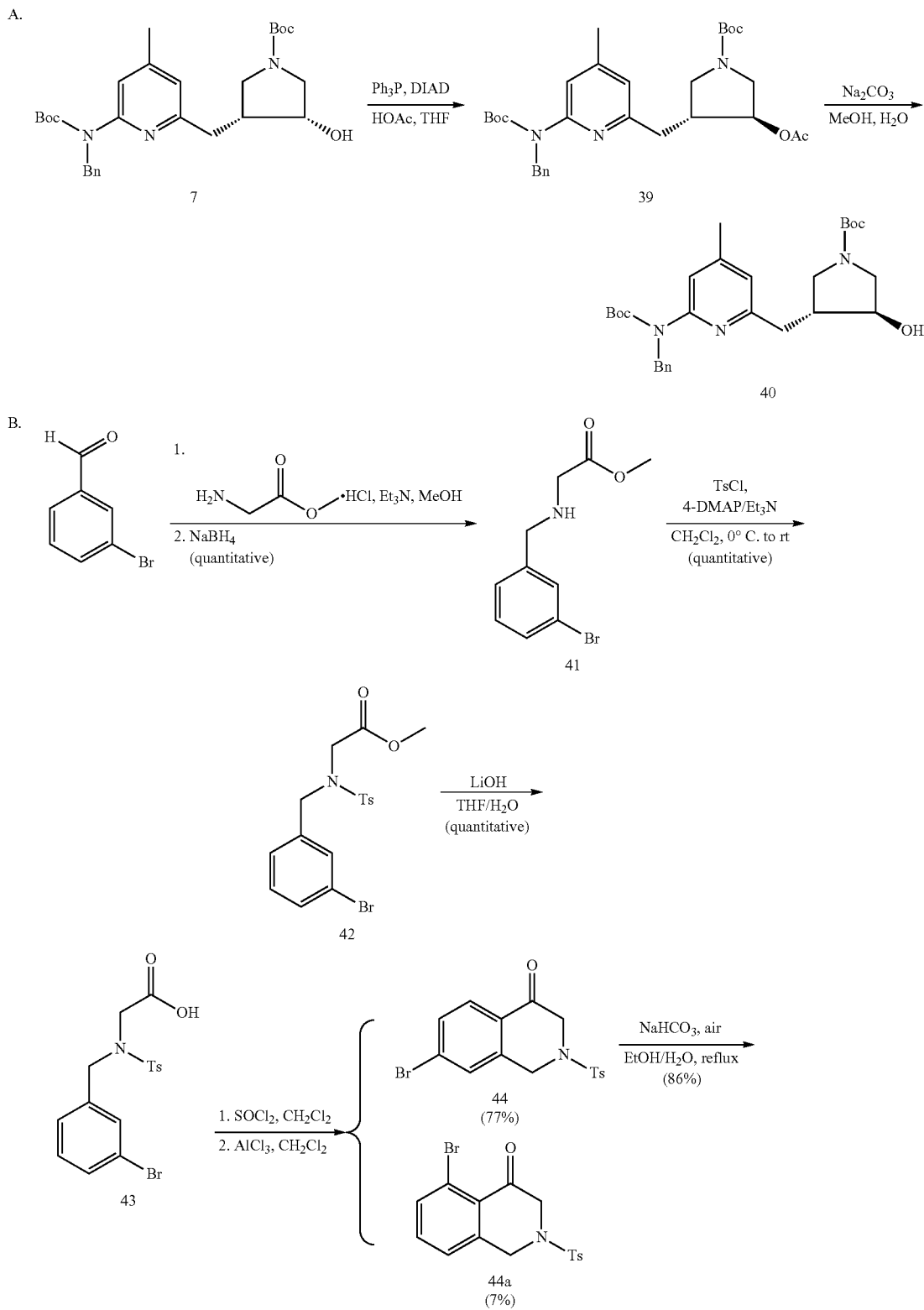

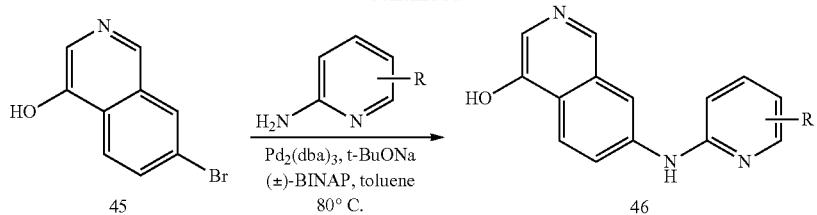
C.
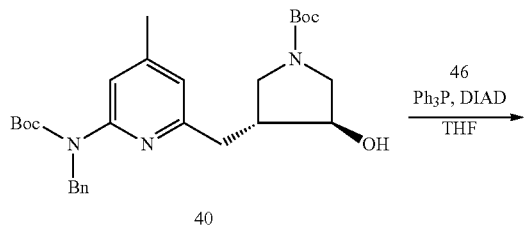
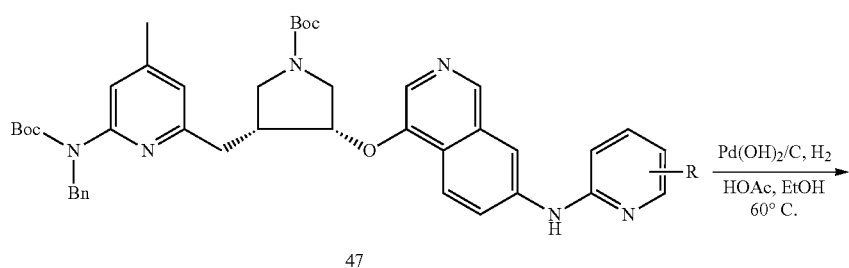
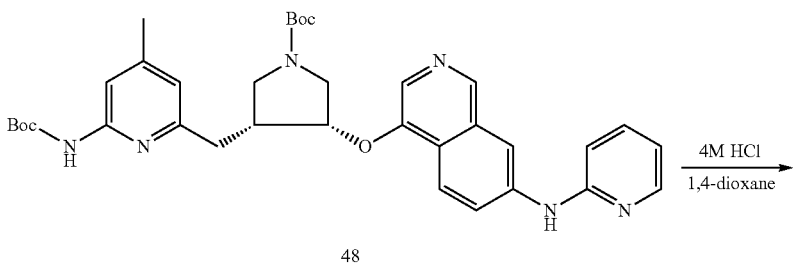
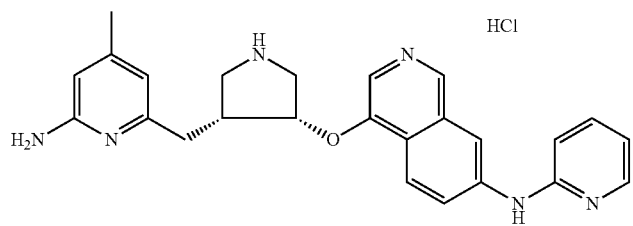

A synthesis of another E series target compound is shown in Schemes 7A-B. 6-hydroxy-1-tetralone was benzyl-protected to generate 50 in a quantitative yield. (Scheme 7A.) The α-monobromination of 50 by cupric bromide afforded 51 in an 83% yield. (At the same time the α,α-dibromo analogue 51a was separated in a 3% yield. The α,β-hydrogen bromide elimination of 51 and subsequent aromatization to generate 52 occurred in a 91% yield.) The α-OH group of 52 was protected with a tert-butyldimethylsilyl (TBDMS) group, and the Bn group was removed by catalytic hydrogenation—both reactions in quantitative yield. The β-OH group of 54 was activated by triflic anhydride in a quantitative yield. A Buchwald-Hartwig reaction generates 56, and a Mitsunobu reaction (Scheme 7B) thereof generates 57. Deprotection of the Bn and Boc groups afford desired final product 59.

Scheme 7.

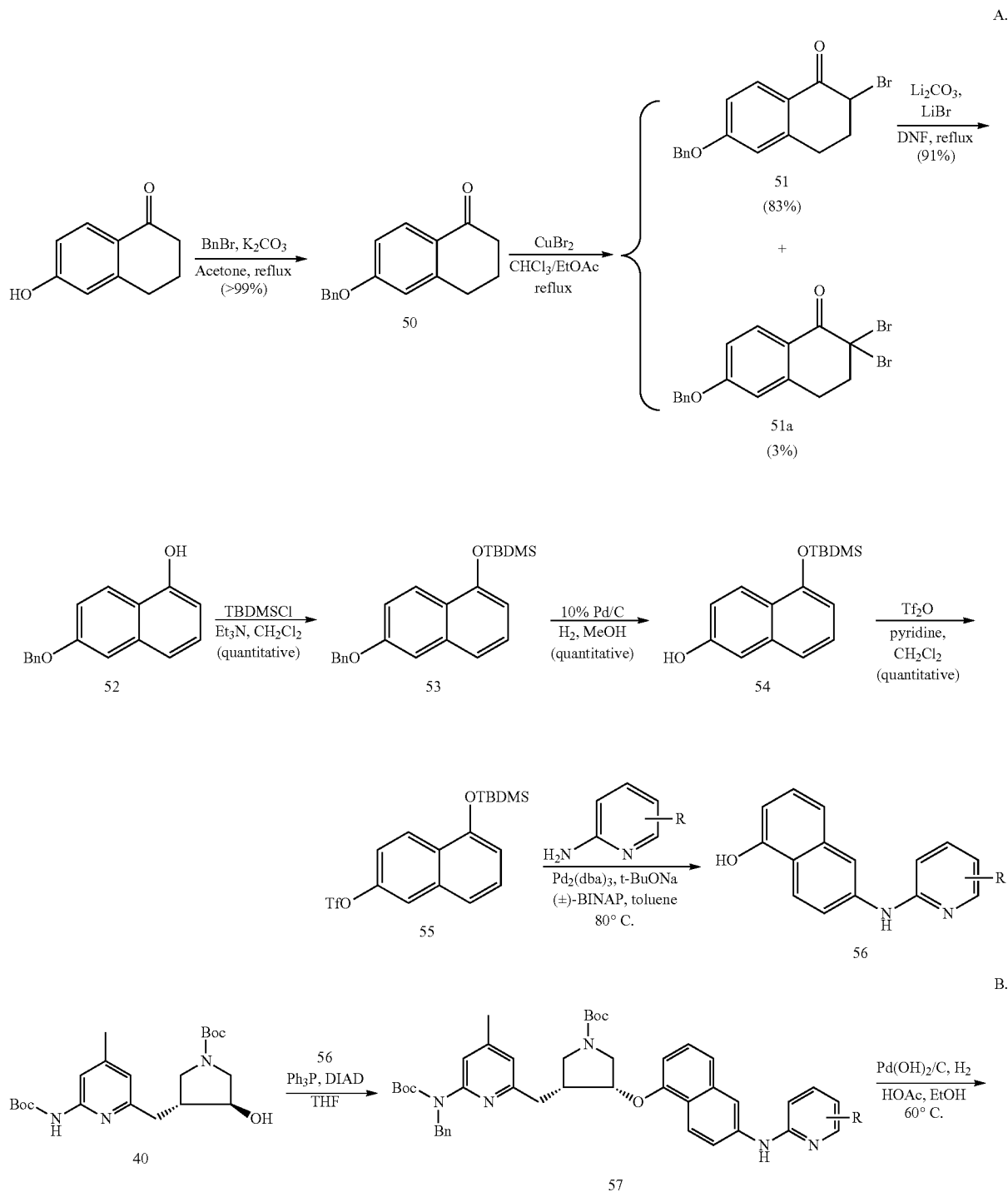

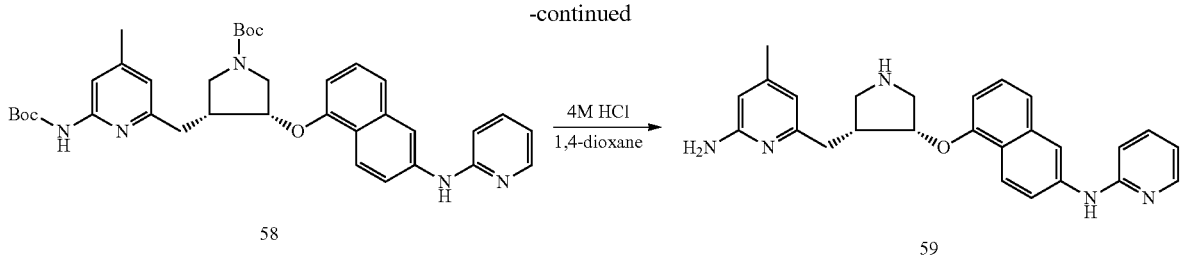

Representative compounds, in accordance with this invention (FIG. 2) were prepared using synthetic techniques of the sort described herein. NOS inhibition assays were undertaken and the results are provided in Table 2, below.

With reference to FIGS. 2 and 3 (and Table 2), several non-limiting compounds were identified as potent, selective nNOS inhibitors:

4-methyl-6-(((3R,4R)-4-((5-(pyridin-2-yl)pentyl)oxy)pyrrolidin-3-yl)methyl)pyridin-2-amine (Ji18);

4-methyl-6-(((3R,4R)-4-((5-(4-methylpyridin-2-yl)pentyl)oxy)pyrrolidin-3-yl)methyl)pyridin-2-amine (Ji19);

6-(((3R,4R)-4-((5-(3-chloro-5-fluorophenyl)pentyl)oxy)pyrrolidin-3-yl)methyl)-4-methylpyridin-2-amine (HH002);

6-(((3R,4R)-4-(((E)-5-(3-fluorophenyl)pent-4-en-1-yl)oxy)pyrrolidin-3-yl)methyl)-4-methylpyridin-2-amine (HH003);

6-(((3R,4R)-4-((5-(3-aminophenyl)pentyl)oxy)pyrrolidin-3-yl)methyl)-4-methylpyridin-2-amine (HH008);

6-(((3R,4R)-4-((5-(3-amino-5-methylphenyl)pentyl)oxy)pyrrolidin-3-yl)methyl)-4-methylpyridin-2-amine (HH009);

4-(((3R,4R)-4((6-amino-4-methylpyridin-2-yl)methyl)pyrrolidin-3-yl)oxy)-N-(pyridin-2-yl)isoquinolin-7-amine (E, e.g., R=H); and 4-methyl-6-(((3R,4R)-4-((6-(pyridin-2-ylamino)naphthalen-1-yl)oxy)pyrrolidin-3-yl)methyl)pyridin-2-amine (F, e.g., R=H).

(Nomenclature for such compounds provided using Chem-BioDraw Ultra, version 12.0.2.1076.)

TABLE 2

List of Ki values and selectivity[a]

| Compounds | nNOS [nM] | eNOS [nM] | iNOS [nM] | n/e[b] | n/i[b] |
| --- | --- | --- | --- | --- | --- |
| Ji18 | 74 | 148890 | 9779 | 2012 | 132 |
| Ji19 | 31 | 45227 | 17305 | 1459 | 558 |
| Ji20 | 9 | 1387 | 491 | 154 | 54 |
| Ji21 | 36 | 5667 | 973 | 157 | 27 |
| Ji22 | 1196 | 146041 | 38080 | 122 | 32 |
| Ji23 | 117 | 4374 | 12438 | 37 | 106 |
| HH001 | 922 | 33800 | 83800 | 37 | 91 |
| HH002 | 230 | 35600 | 106000 | 155 | 461 |
| HH003 | 637 | 77000 | 35100 | 121 | 55 |
| HH004 | 9057 | 34000 | 468500 | 4 | 52 |
| HH005 | 15402 | 69000 | 133800 | 4 | 9 |
| HH008 | 30 | 33500 | 18600 | 1117 | 619 |
| HH009 | 38 | 26100 | 6500 | 687 | 172 |

[a] $K_M$ values of rat nNOS, 1.3 µM; murine iNOS, 8.2 µM; bovine eNOS, 1.7 µM). $K_i = IC_{50}/(1 + [S]/K_M)$.
[b] The ratio of $K_i$ (eNOS or iNOS) to nNOS; the compounds were evaluated for in vitro inhibition against three NOS isozymes: rat nNOS, bovine eNOS and marine iNOS using known literature methods. (See, Hevel, J. M.; Marletta, M. A. Nitric-oxide synthase assays. Method Enzymol. 1994, 233, 250-258; see, also, examples 58-59 of U.S. Pat. No. 7,994,326 and U.S. Pat. No. 7,740,790 - each of which is incorporated herein by reference in its entirety.)

From crystal complex studies (not shown), it was determined that Ji18 and Ji19 have the same binding mode as that of Ji10, discussed above. Note, Ji18 and Ji19 do not have a secondary amine between the oxygen and the pyridine ring, on the side chain, above the heme. Several observations can be made:

Ji20 has higher nNOS potency, but lower nNOS selectivity over eNOS, compared with Ji19; Ji21, a (3S, 4S) compound, binds predominantly through a flipped binding mode; and Ji22 and Ji23 can be used to explore the dipole-dipole interaction in the deep pocket of the NOS substrate-binding site.

More generally, as demonstrated below as would be understood by those skilled in the art, the structure of such a compound is limited only by choice, commercial or synthetic availability of starting material or reagent, enroute to a pyridine substructure (I), pyrrolidine substructure (II) and/or lipophilic tail substructure (III), such substructures as are discussed more fully below and/or in U.S. Pat. Nos. 7,470,790 and 7,994,326—each of which is incorporated herein by reference in its entirety. Accordingly, various compounds of this invention can, optionally, comprise various other substructures I, II and/or III or other moieties and/or substituents thereof, such as the substructures, moieties and/or groups described in the aforementioned incorporated references. As such, with respect to the broader aspects of this invention, the present compounds are without stereochemical limitation. Where such compounds and/or their intermediates are available as racemic mixtures, the respective isomers can be resolved. Likewise, as such compounds are diastereomers, the corresponding enantiomers can be separated. Accordingly, any such stereocenter can be (S) or (R) with respect to any other stereocenter(s), whether such a compound is present as a salt, hydrate and/or solvate thereof. Regardless, any such compound(s) can be provided as part of a pharmaceutical composition comprising a pharmaceutically-acceptable carrier component for use in conjunction with a method or medicament of this invention.

The present invention can also, as would be understood by those skilled in the art, be extended to or include methods using or in conjunction with a pharmaceutical composition comprising an inhibitor compound of the sort described herein and a physiologically or otherwise suitable formulation. In a some embodiments, the present invention includes one or more NOS inhibitors, as set forth above, formulated into compositions together with one or more physiologically tolerable or acceptable diluents, carriers, adjuvants or vehicles that are collectively referred to herein as carriers. Compositions suitable for such contact or administration can comprise physiologically acceptable sterile aqueous or non-aqueous solutions, dispersions, suspensions or emulsions. The resulting compositions can be, in conjunction with the various methods described herein, for administration or contact with a nitric oxide synthase expressed or otherwise present. Whether or not in conjunction with a pharmaceutical composition, "contacting" means that a nitric oxide synthase and one or more inhibitor compounds are brought together for purpose of binding and/or complexing such an inhibitor compound with the enzyme. Amounts of a compound effective to inhibit a nitric oxide synthase may be determined empirically, and making such determinations is within the skill in the art. Inhibition or otherwise affecting nitric oxide synthase activity includes both reduction and/or mitigation, as well as elimination of NOS activity and/or nitric oxide production.

It is understood by those skilled in the art that dosage amount will vary with the activity of a particular inhibitor compound, disease state, route of administration, duration of treatment, and like factors well-known in the medical and pharmaceutical arts. In general, a suitable dose will be an amount which is the lowest dose effective to produce a therapeutic or prophylactic effect. If desired, an effective dose of such a compound, pharmaceutically-acceptable salt thereof, or related composition may be administered in two or more sub-doses, administered separately over an appropriate period of time.

Methods of preparing pharmaceutical formulations or compositions include the step of bringing an inhibitor compound into association with a carrier and, optionally, one or more additional adjuvants or ingredients. For example, standard pharmaceutical formulation techniques can be employed, such as those described in Remington's Pharmaceutical Sciences, Mack Publishing Company, Easton, Pa.

Regardless of composition or formulation, those skilled in the art will recognize various avenues for medicament administration, together with corresponding factors and parameters to be considered in rendering such a medicament suitable for administration. Accordingly, with respect to one or more non-limiting embodiments, the present invention provides for use of one or more neuronal nitric oxide synthase inhibitor compounds for the manufacture of a medicament for therapeutic use in the treatment or the prevention of one or more neurodegenerative diseases.

We claim:
1. A nitric oxide synthase inhibitor compound of a formula

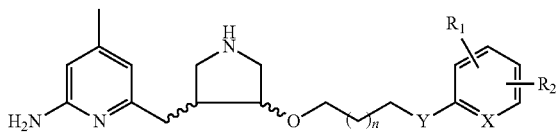

wherein n is selected from 0 and 1; Y is selected from $CH_2$, O, NH, $CH_2O$, $CH_2NH$, $CH_2CH_2$ and CH=CH moieties; X is selected from N and CH; and $R_1$ and $R_2$ are independently selected from H, amono, methyl, methoxy, fluoro, chloro, and mono-, di- and trifluoromethyl, and mono-, di, and trichloromethyl substituents, and combinations thereof, or a salt thereof.

2. The compound of claim 1 wherein n is 1, Y is $CH_2CH_2$ and X is N.

3. The compound of claim 2 wherein $R_1$ is selected from H and a 4-methyl substituent; and $R_2$ is independently selected from H and a 2-amino substituent.

4. The compound of claim 3 wherein said compound is an ammonium salt.

5. The compound of claim 4 wherein said ammonium salt has a counterion that is a conjugate base of a protic acid.

6. A nitric oxide synthase inhibitor compound of a formula

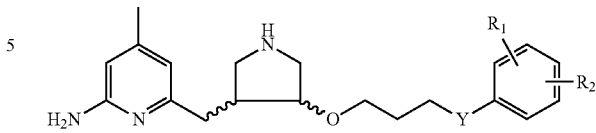

wherein Y is selected from $CH_2CH_2$ and CH=CH moieties; and $R_1$ and $R_2$ are independently selected from H, Cl and F, or a salt thereof.

7. The compound of claim 6 wherein at least one of $R_1$ and $R_2$ is F.

8. The compound of claim 7 wherein $R_1$ is selected from H and a 3-chloro substitutent; and $R_2$ is a 5-fluoro substituent.

9. The compound of claim 8 wherein said compound is an ammonium salt.

10. The compound of claim 9 wherein said ammonium salt has a counterion that is a conjugate base of a protic acid.

11. A compound selected from
6-(((3R,4R)-4-((5-(3-chloro-5-fluorophenyl)pentyl)oxy)pyrrolidin-3-yl)methyl)-4-methylpyridin-2-amine (HH002); and
6-(((3R,4R)-4-(((E)-5-(3-fluorophenyl)pent-4-en-1-yl)oxy)pyrrolidin-3-yl)methyl)-4-methylpyridin-2-amine (HH003).

12. A pharmaceutical composition comprising the compound of claim 6.

13. A nitric oxide synthase inhibitor compound of a formula

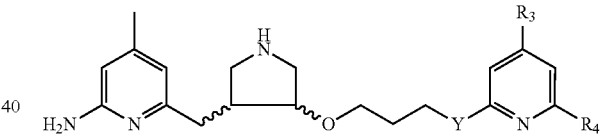

wherein Y is selected from $CH_2CH_2$ and CH=CH moieties; $R_3$ is selected from H and $CH_3$; and $R_4$ is selected from H and $NH_2$, or a salt thereof.

14. The compound of claim 13 wherein Y is $CH_2CH_2$, and one of $R_3$ and $R_4$ is not H.

15. The compound of claim 14 wherein $R_3$ is selected from H and a 4-methyl substituent; and $R_4$ is a 2-amino substituent.

16. The compound of claim 15 wherein said compound is an ammonium salt.

17. The compound of claim 16 wherein said ammonium salt has a counterion that is a conjugate base of a protic acid.

18. A compound selected from
4-methyl-6-(((3R,4R)-4-((5-(pyridin-2-yl)pentyl)oxy)pyrrolidin-3-yl)methyl)pyridin-2-amine;
4-methyl-6-(((3R,4R)-4-((5-(4-methylpyridin-2-yl)pentyl)oxy)pyrrolidin-3-yl)methyl)pyridin-2-amine;
6-(((3R,4R)-4-((5-(3-aminophenyl)pentyl)oxy)pyrrolidin-3-yl)methyl)-4-methylpyridin-2-amine; and
6-(((3R,4R)-4-((5-(3-amino-5-methylphenyl)pentyl)oxy)pyrrolidin-3-yl)methyl)-4-methylpyridin-2-amine.

19. A pharmaceutical composition comprising the compound of claim 13.

20. A nitric oxide synthase inhibitor compound of a formula

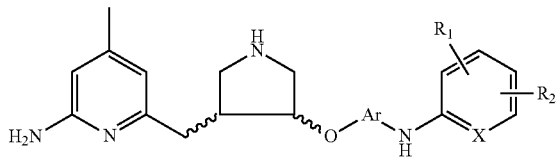

wherein Ar is selected from naphthalenylene and isoquinolinylene moieties; X is selected from CH and N; $R_1$ is selected from H and $CH_3$; and $R_2$ is independently selected from H and $NH_2$, and or salt thereof.

21. The compound of claim 20 wherein X is N.

22. The compound of claim 21 wherein $R_1$ is selected from H and a 4-methyl substituent; and $R_2$ is a 2-amino substituent.

23. The compound of claim 22 wherein said compound is an ammonium salt.

24. The compound of claim 23 wherein said ammonium salt has a counterion that is a conjugate base of a protic acid.

25. A compound selected from
4-(((3R,4R)-4-((6-amino-4-methylpyridin-2-yl)methyl)pyrrolidin-3-yl)oxy)-N-(pyridin-2-yl)isoquinolin-7-amine; and
4-methyl-6-(((3R,4R)-4-((6-(pyridin-2-ylamino)naphthalen-1-yl)oxy)pyrrolidin-3-yl)methyl)pyridin-2-amine.

26. A pharmaceutical composition comprising the compound of claim 20.

27. A method of inhibiting a nitric oxide synthase, said method comprising contacting a nitric oxide synthase with an effective amount of a compound of claim 1.

28. The method of claim 27 wherein n is 1, Y is $CH_2CH_2$ and X is N.

29. The method of claim 28 wherein said compound is selected from
4-methyl-6-(((3R,4R)-4-((5-(pyridin-2-yl)pentyl)oxy)pyrrolidin-3-yl)methyl)pyridin-2-amine;
4-methyl-6-(((3R,4R)-4-((5-(4-methylpyridin-2-yl)pentyl)oxy)pyrrolidin-3-yl)methyl)pyridin-2-amine;
6-(((3R,4R)-4-((5-(3-aminophenyl)pentyl)oxy)pyrrolidin-3-yl)methyl)-4-methylpyridin-2-amine; and
6-(((3R,4R)-4-((5-(3-amino-5-methylphenyl)pentyl)oxy)pyrrolidin-3-yl)methyl)-4-methylpyridin-2-amine.

30. The method of claim 29 wherein said compound is provided in a pharmaceutical composition.

* * * * *

UNITED STATES PATENT AND TRADEMARK OFFICE
CERTIFICATE OF CORRECTION

PATENT NO.         : 8,557,552 B2
APPLICATION NO.    : 13/441683
DATED              : October 15, 2013
INVENTOR(S)        : Richard B. Silverman, Haitao Ji and He Huang Page 1 of 1

It is certified that error appears in the above-identified patent and that said Letters Patent is hereby corrected as shown below:

In the claims:

Column 35, line 54

"selected from H, amono, methyl, methoxy, fluoro, chloro, and" should read --selected from H, amino, methyl, methoxy, fluoro, chloro, and--.

Column 37, line 17

"$NH_2$, and or salt thereof." should read --$NH_2$, and a salt thereof.--.

Signed and Sealed this
Twentieth Day of May, 2014

Michelle K. Lee
*Deputy Director of the United States Patent and Trademark Office*